United States Patent
Modglin

(10) Patent No.: US 10,098,774 B2
(45) Date of Patent: Oct. 16, 2018

(54) RIGID BRACES WITH TENSIONING SYSTEM

(71) Applicant: DeRoyal Industries, Inc., Powell, TN (US)

(72) Inventor: Michael D. Modglin, Braselton, GA (US)

(73) Assignee: DeRoyal Industries, Inc., Powell, TN (US)

( * ) Notice: Subject to any disclaimer, the term of this patent is extended or adjusted under 35 U.S.C. 154(b) by 494 days.

(21) Appl. No.: 13/768,060

(22) Filed: Feb. 15, 2013

(65) Prior Publication Data

US 2013/0245522 A1  Sep. 19, 2013

Related U.S. Application Data

(60) Provisional application No. 61/611,147, filed on Mar. 15, 2012.

(51) Int. Cl.
*A61F 5/01* (2006.01)
*A61F 5/02* (2006.01)

(52) U.S. Cl.
CPC .............. *A61F 5/01* (2013.01); *A61F 5/0102* (2013.01); *A61F 5/02* (2013.01)

(58) Field of Classification Search
CPC ...... A61F 5/05; A61F 5/05841; A61F 5/0585; A61F 5/05858; A61F 5/05866; A61F 5/01; A61F 5/0102; A61F 5/0123; A61F 5/0127; A61F 5/013; A61F 2005/0132; A61F 2005/0165; A61F 2005/0167
USPC .......................... 602/16, 20, 23, 26; 128/882
See application file for complete search history.

(56) References Cited

U.S. PATENT DOCUMENTS

| | | | | |
|---|---|---|---|---|
| 4,633,867 A * | 1/1987 | Kausek et al. | | 602/26 |
| 4,665,908 A * | 5/1987 | Calkin | | 128/870 |
| 5,599,288 A * | 2/1997 | Shirley et al. | | 602/26 |
| 7,156,819 B2 * | 1/2007 | Sieller et al. | | 602/21 |
| 7,311,687 B2 * | 12/2007 | Hoffmeier et al. | | 602/26 |
| 7,654,972 B2 * | 2/2010 | Alleyne | | A61F 5/026 602/19 |
| 7,806,842 B2 | 10/2010 | Stevenson et al. | | |
| 7,901,371 B1 | 3/2011 | Vayntraub | | |
| 8,951,217 B2 * | 2/2015 | Joseph | | 602/7 |
| 2006/0173391 A1 * | 8/2006 | Bodenschatz | | A61F 5/058 602/12 |
| 2008/0066272 A1 * | 3/2008 | Hammerslag et al. | | 24/712 |

(Continued)

FOREIGN PATENT DOCUMENTS

EP  1238640 A1  11/2002
JP  2004358196 A  12/2004

(Continued)

OTHER PUBLICATIONS

International Search Report and Written Opinion, PCT/US13/30110, dated May 21, 2013—19 pages.

(Continued)

*Primary Examiner* — Alireza Nia
*Assistant Examiner* — Camtu Nguyen
(74) *Attorney, Agent, or Firm* — Luedeka Neely Group, PC

(57) ABSTRACT

A brace for application to a body joint, the brace including a substantially rigid brace substrate and a tensioning system for imparting tension to the substrate for adjusting the contour or angulation of the substrate.

9 Claims, 15 Drawing Sheets

(56) References Cited

U.S. PATENT DOCUMENTS

| 2008/0249448 | A1  | 10/2008 | Stevenson et al. |
| 2008/0319362 | A1* | 12/2008 | Joseph ..................... A61F 5/01 |
| | | | 602/7 |
| 2009/0054819 | A1  | 2/2009  | Einarsson |
| 2009/0118656 | A1  | 5/2009  | Ingimundarson et al. |

FOREIGN PATENT DOCUMENTS

| WO | 2010059642 A2 | 5/2010 |
| WO | 2010059642 A3 | 5/2010 |

OTHER PUBLICATIONS

Nariyama Satoshi, Lumbago Preventive Wearing Implement, Publication 2004358196 Abstract dated Dec. 24, 2004.
EESR, PCT/US2013-030110 dated Oct. 19, 2015 (7 pages).

* cited by examiner

RIGID BRACES WITH TENSIONING SYSTEM

CROSS-REFERENCE TO RELATED APPLICATION

This application claims priority to U.S. Provisional Application No. 61/611,147 entitled RIGID BRACES WITH TENSIONING SYSTEM, filed, Mar. 15, 2012, incorporated by reference herein in its entirety.

FIELD

This disclosure relates to the field of orthopedic bracing. More particularly, this disclosure relates to rigid orthopedic braces incorporating cable reels that enable the bracing to be adjustably contoured to a desired angulation.

BACKGROUND

Improvement is desired in the provision of braces and splints for orienting a body joint in a desired orientation.

In particular, what is desired is a rigid splint or brace that maintains the joint in a static position, that is, permits virtually no range of motion, yet can be adjusted to position the joint in a desired angular orientation for a period of time and then able to be periodically readjusted to change the orientation as desired. Such braces or splints would be particularly suitable in treating of various spinal pathologies or other joint pathologies where extension or flexion of the spinal segments or other joint components is prescribed, or for the contracture of a body joint to restore or assist normal range of motion.

Also desired are braces as described, but which further offer the option of a dynamic function and adjustably providing a degree of extension or flexion or the like for a body joint.

SUMMARY

The above and other needs are met by a brace for application to a body joint, brace for application to a body joint, the brace including a substantially rigid brace member that substantially maintains its shape absent application of a substantial bending force and provides biomechanical support, stabilization and/or immobilization to the body joint.

A tensioning system is connected to the brace member and includes a tensionable member and a tensioning member each operatively associated with the brace member. The tensioning member is operable to adjustably impart tension to the tensionable member for applying a force to the brace member for adjusting the contour or angulation of the brace to change the shape of the brace as a function of the tension applied to the tensionable member.

In another aspect, the brace includes a substantially rigid brace substrate configured for application to a body joint and that substantially maintains a desired orientation of the brace structure absent application of a substantial bending force and provides biomechanical support, stabilization and/or immobilization to the body joint. A cable reel is mounted to a first portion of the brace substrate and a cable is operatively associated with the cable reel to wind and unwind the cable from the reel. A cable guide is fixed to the brace at a location apart from the cable reel, with the cable being trained through the cable guide and connected to the cable reel.

When the cable is substantially untensioned the brace structure is configured in a substantially linear orientation. When the cable reel is operated to tension the cable, the cable applies a force to the brace structure and the brace structure changes its orientation and becomes angulated to a non-linear orientation as a function of the tension applied to the cable by the cable reel.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
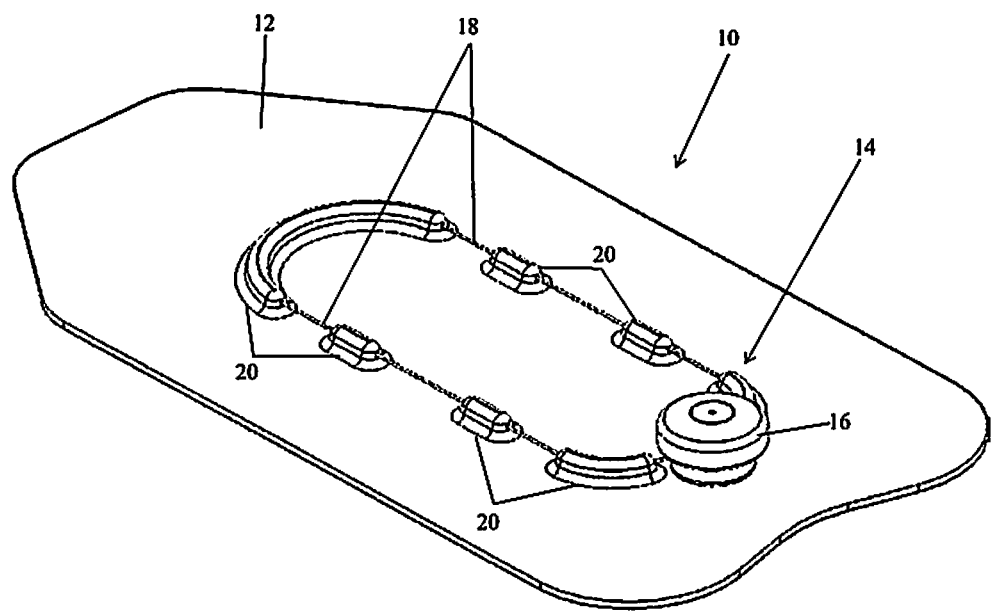
FIGS. 1-4 show a back brace according to the disclosure.

The disclosure relates to substantially rigid orthopedic braces incorporating cable reels that enable the bracing to be adjustably contoured to a desired angulation. The brace may be configured to cooperate with various body joints, such as the back, wrist/hand, ankle, and knee.

With reference to FIGS. 1-4, there is shown a back brace 10 having a substantially rigid brace substrate 12 and a cable reel system 14 for adjusting the contour or angulation of the substrate 12.

The substrate 12 may be a substantially rigid polymeric material that substantially maintains its shape absent application of substantial force thereto to bend. That is, the material is sufficiently biomechanically rigid to provide the desired amount of biomechanical support, stabilization and/or immobilization of the affected body part or area. If desired, to promote bending at desired locations of the substrate 12, the substrate may include a hinge, such as a living hinge 12*a*. Accordingly, it will be understood that "substantially rigid" as used herein refers to and includes semi-rigid materials and the like that may have some flexure, but which substantially maintain their shape absent application of a substantial bending force and provide a desired amount of biomechanical support, stabilization and/or immobilization of the affected body part or area.

The cable reel system 14 includes a cable reel 16 having a cable 18 extending from the reel 16, and cable guides 20 affixed to a portion of the brace 10. The reel 16 is a spring-loaded rotating spool that winds or unwinds the cable 18 to either tension or untension the cable 18. Suitable devices to use for the reel 20 are cable reel devices available under the name BOA from Boa Technology, Inc. of Denver, Colo., and described in U.S. Pat. Nos. 7,954,204 and 7,992,261, incorporated by reference in their entireties. The reel 16 may be mounted to the substrate 12, as by use of plastic rivets, and the like.

Figure 5:
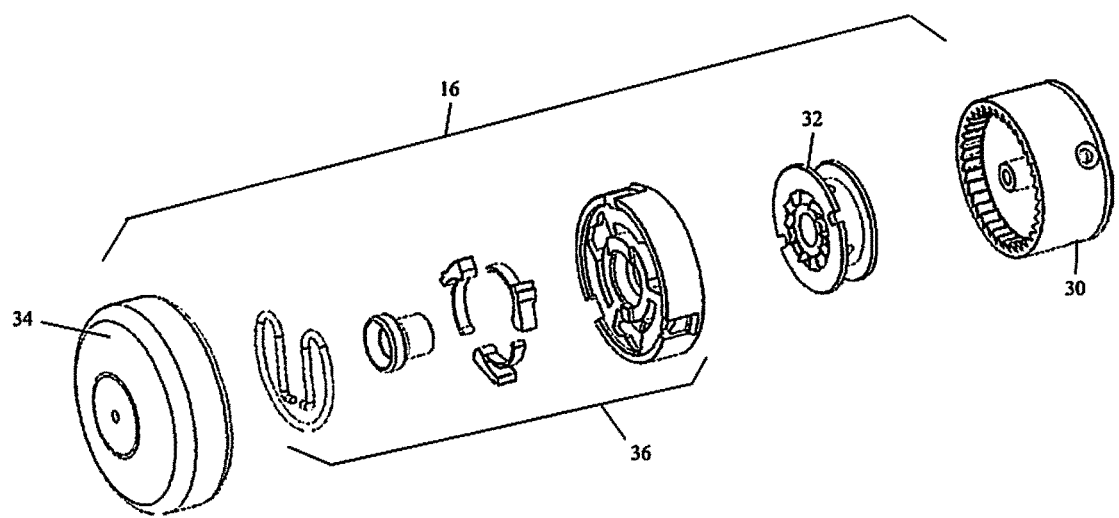
FIG. 5 is an exploded perspective view of a cable reel component of the back brace of FIGS. 1-4.
Figure 6:
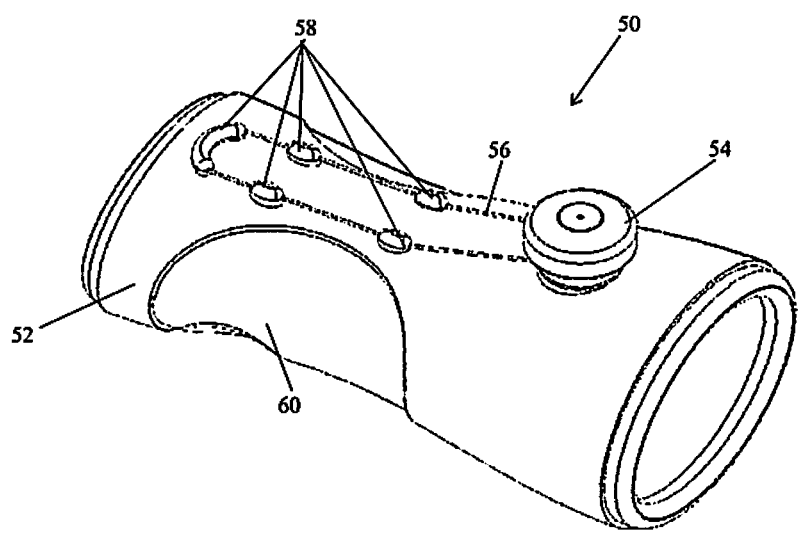
FIGS. 6-9 show a wrist brace according to the disclosure.
Figure 7:
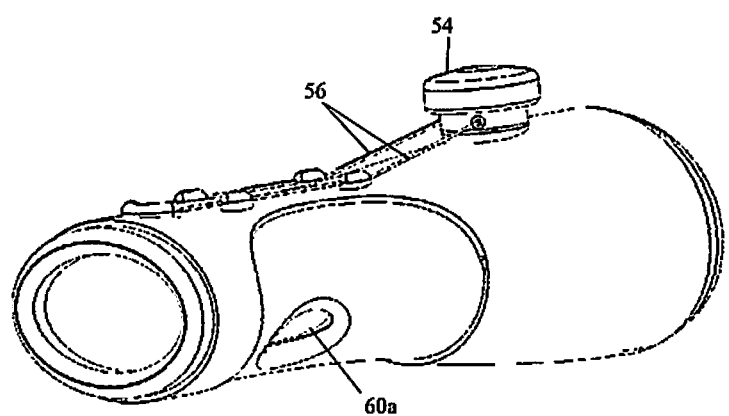
Figure 8:
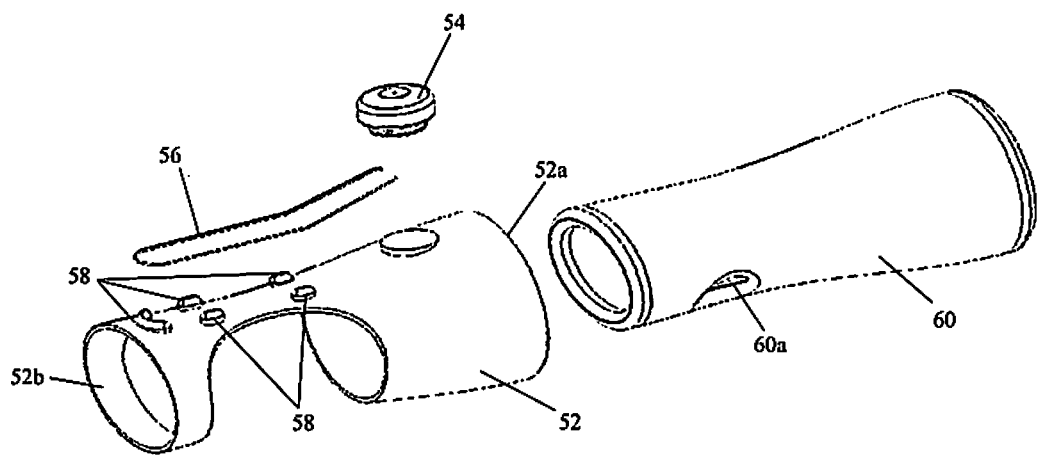

With reference to FIG. 5, the cable reel 16 is a rotating spool that winds or unwinds the cable 18 and, preferably includes a toothed housing 30 configured for receiving the ends of the cable 18, each end rotationally linked to a spool 32 contained within the housing 30. A knob 34 having a spring-loaded assembly 36 cooperates with the housing 30 and the spool 32 for manually winding the cable 18 around the spool 32. The knob 34 and spring-loaded assembly 36 cooperate to engage the spool 32 with the housing 30 to provide a ratchet feature for winding the spool 32 when the knob 34 is turned in one direction to tension the cable 18, and for releasing the spool 32 to untension the cable 18. The cable 18 may be a nylon coated, stainless steel cable.

Figure 3:
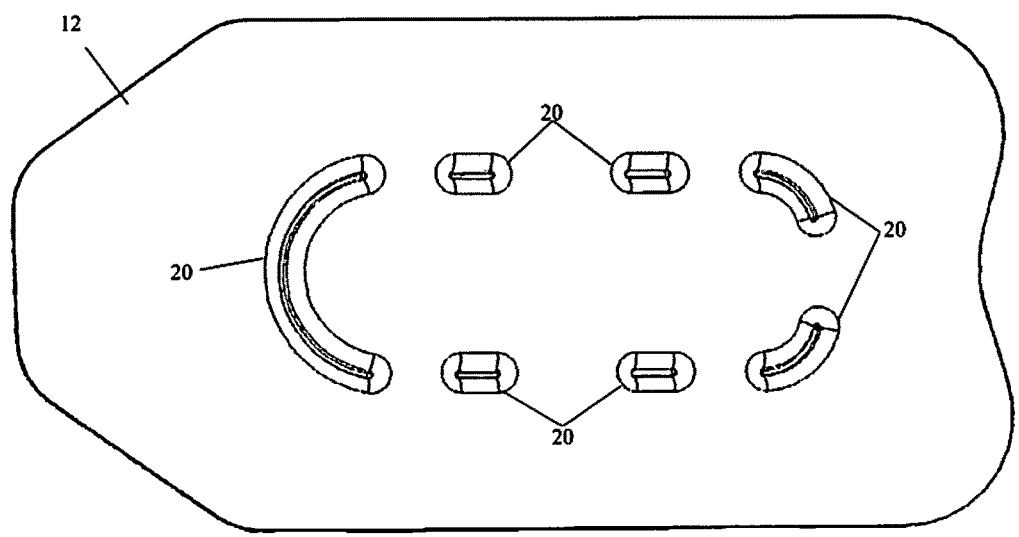
Figure 4:
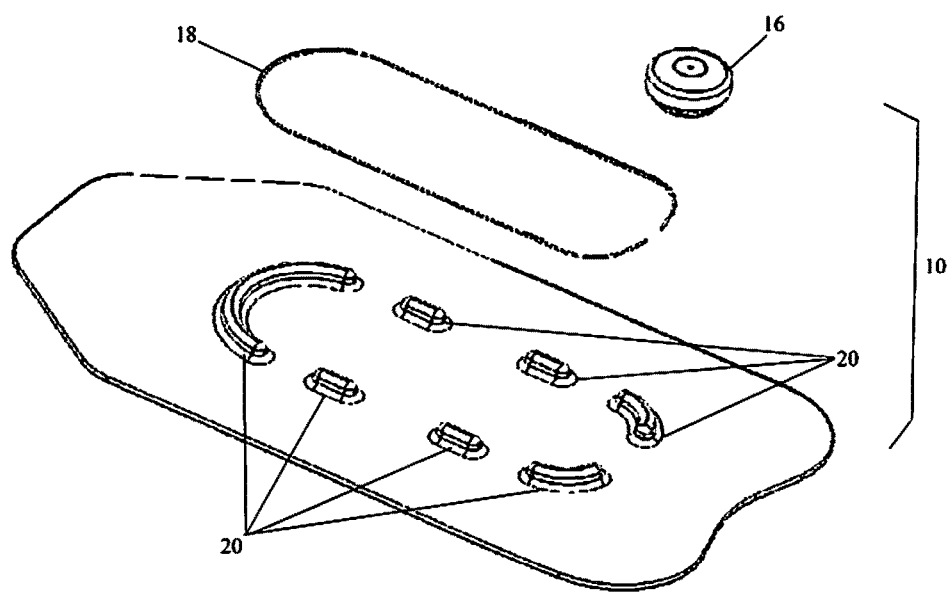

The guides 20 may be continuous or discontinuous and are located so as to train the cable 18 in a desired manner to achieve a desired bending of brace substrate 12 compatible with the back to impart a desired angulation to the back of the patient wearing the brace 10. The guides 20 as shown are molded with the substrate 12, with the guides 20 projecting from one surface of the substrate 12. Thus, the guides appear as negatives or void spaces on the opposite surface of the substrate 12 (FIG. 3). The guides 20 may be otherwise configured and may be routed so as to not be visible. For example, the substrate 12 may be a laminate with internal guides located within the laminate.

Figure 2:
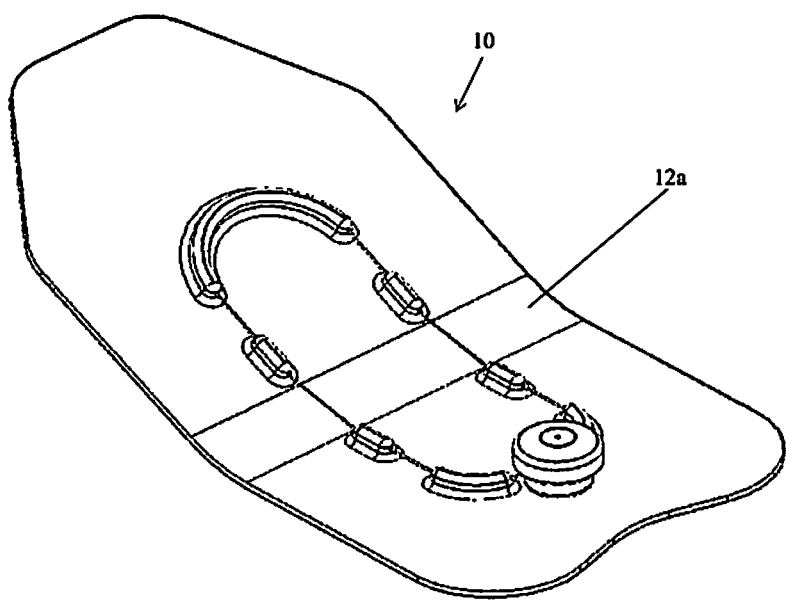

The brace 10 is shown in FIG. 2 with the cable 18 tensioned to provide a desired bending of the brace 10. In this regard, it will be understood that if the tension were removed from the cable 18, the substrate 12 would return to a substantially linear orientation.

With reference to FIGS. 6-9, there is shown a wrist brace 50 including a rigid substrate 52 configured for installation on a wrist of a user and including an opening 52a for receiving the forearm of a patient and an opening 52b for passage of the hand of the user. A central portion of the sidewall of the substrate 52 is desirably open for locating a thumb of the patient. The brace 50 has mounted thereon a cable reel 54 having a cable 56, and cable guides 58. The wrist brace 50 may also include an inner sleeve 60. The inner sleeve 60 may have an aperture 60a for receiving the thumb of the patient and is made of a soft and flexible material, such as neoprene, to cushion and provide the user comfort from the rigid substrate 52.

Figure 9:
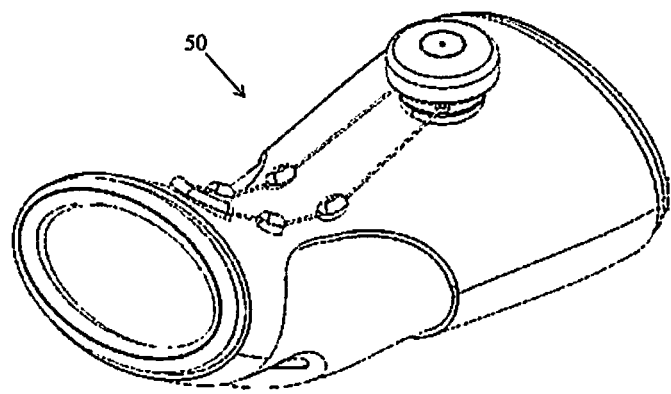
Figure 10:
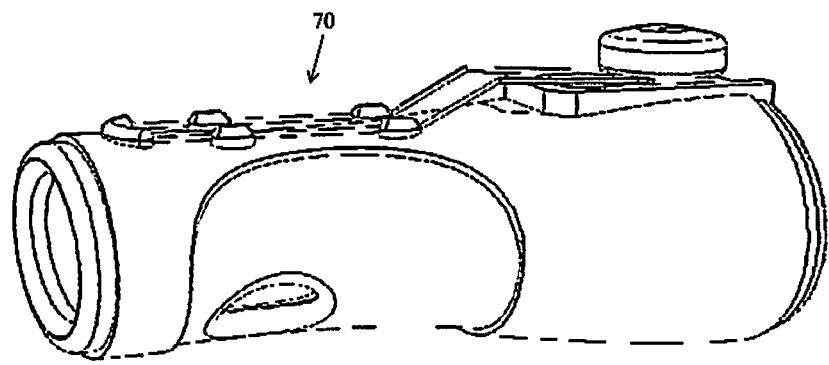
FIGS. 10-16 show an alternate embodiment of a wrist brace according to the disclosure.
Figure 11:
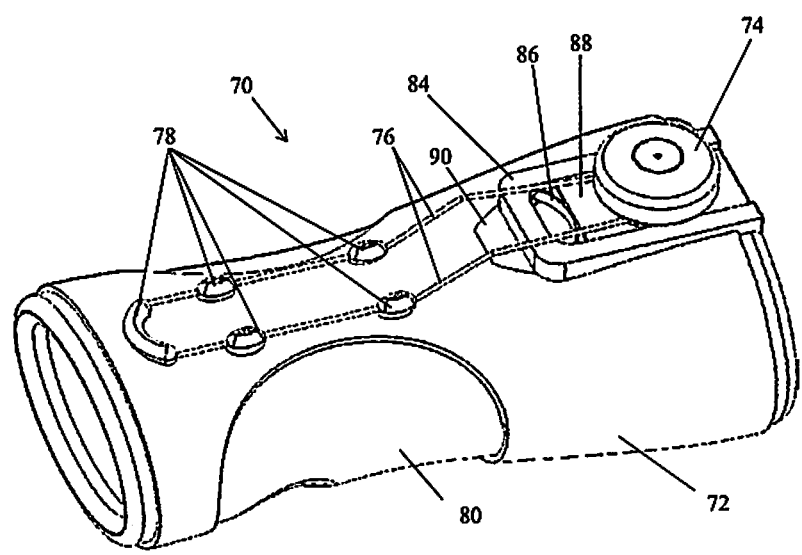
Figure 12:
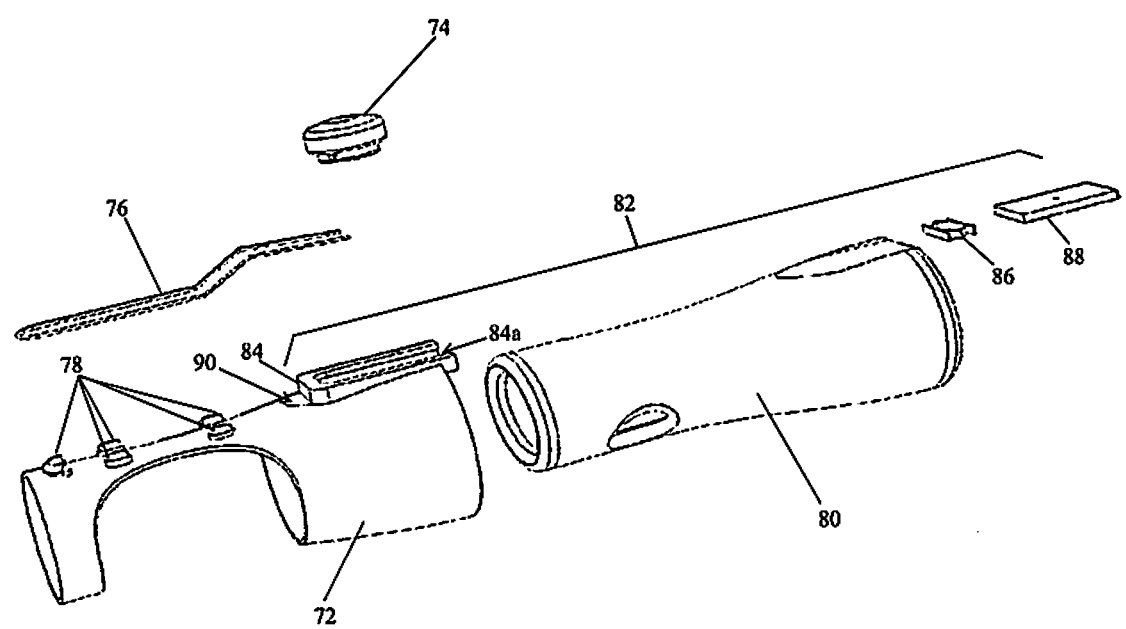

The reel 54 and its cable 56 and guides 58 are located for tightening the brace 50 about the wrist of the patient, and for desirably bending the substrate 52 to impart a desired angulation to the wrist of the patient wearing the brace. As seen in FIG. 9, the cable 56 is tensioned to provide an upward bending of the substrate 52. It will be appreciated that the brace 50 can also be configured to provide other desired bending or angulation characteristics compatible with the wrist joint. The substrate 52 may be made of the same material as described for the substrate 12. The reel 54 is substantially similar to the reel 16, and the guides 58 are substantially similar to the guides 20 described herein.

With reference to FIGS. 10-16, there is shown an alternate embodiment of a wrist brace 70. The brace 70 is substantially similar to the brace 50, except the brace 70 is configured to have the cable reel thereof yieldably mounted thereon. The brace 70 includes a rigid substrate 72 configured for installation on a wrist of a user. The brace 70 has mounted thereon a cable reel 74 having a cable 76, and cable guides 78. The wrist brace 50 may also include an inner sleeve 80. A yieldable mounting system 82 is provided for yieldably positioning the cable reel 74 relative to the rigid substrate 72.

The mounting system 82 includes a base 84 having a blind channel 84a within which is located a bias member 86, such as a flat compression spring, and a movable member 88. The base 84 is a u-shaped member fixedly mounted to the rigid substrate 72. The rigid substrate 72 may include a depression 90 or other topography for receiving the base 84. The channel 84a permits the movable member 88 to slide, with the bias member 86 being located between the movable member 88 and the closed or blind end of the channel 84a. The cable reel 74 is fixedly mounted to the movable member 88. The degree of tension imparted to the cable 76 by the cable reel 74 determines the degree of compression of the bias member 86 so as to yieldably mount the cable reel 74 to the substrate 72.

Figure 13:
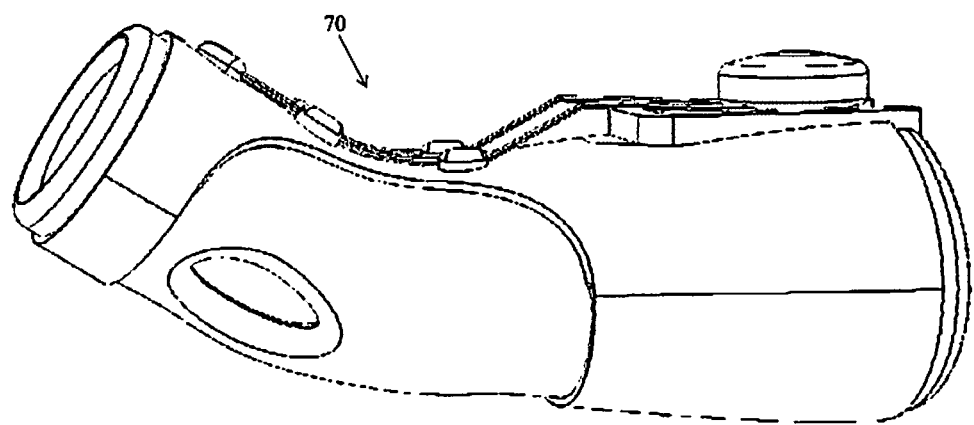
Figure 14:
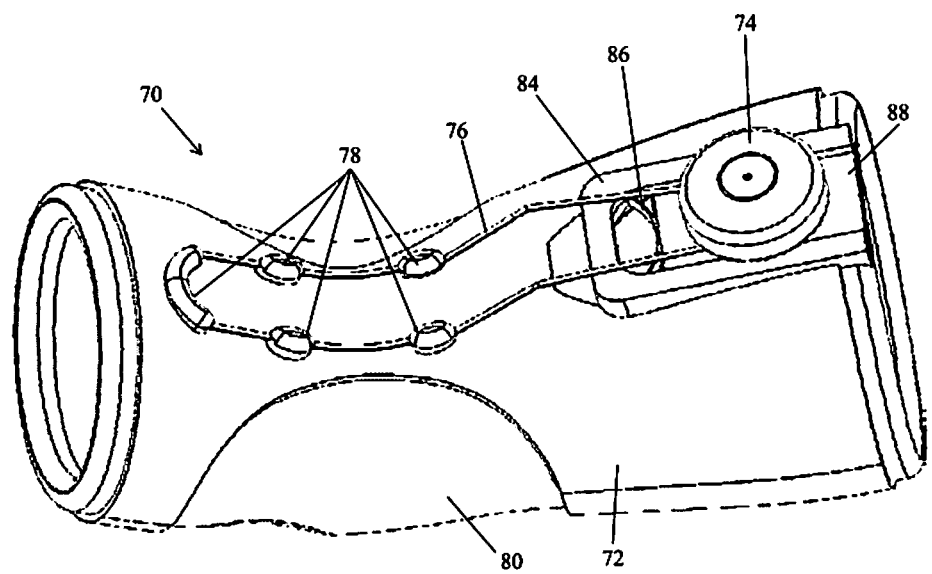
Figure 15:
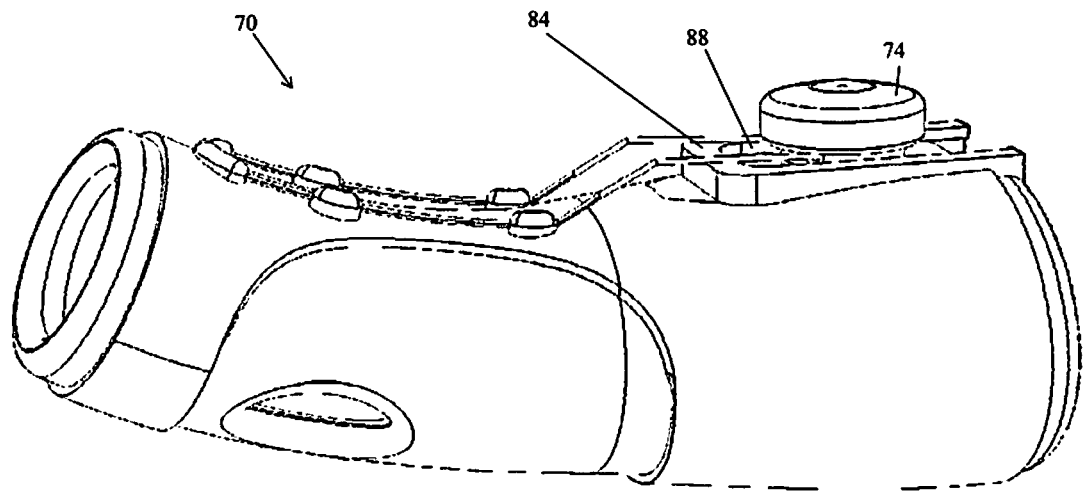
Figure 16:
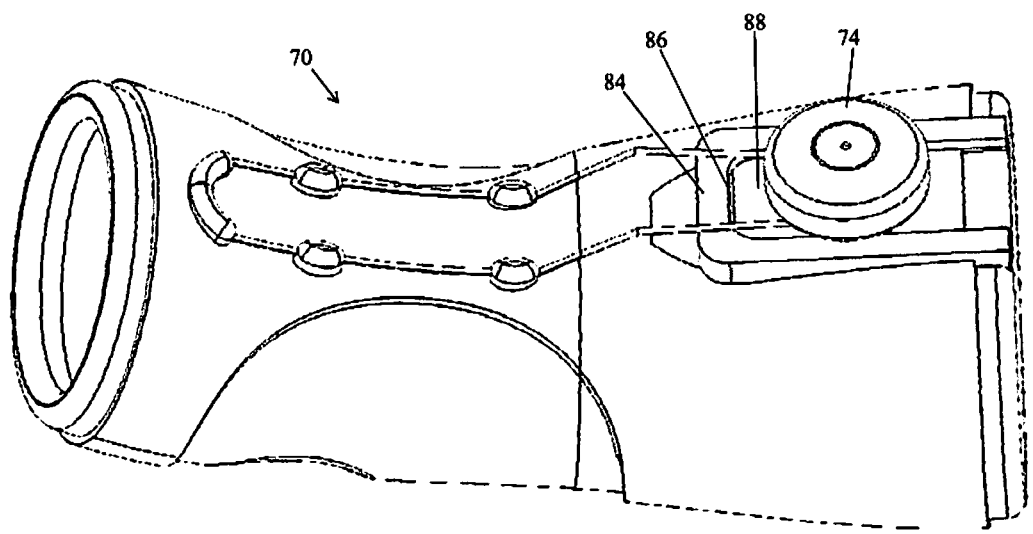
Figure 17:
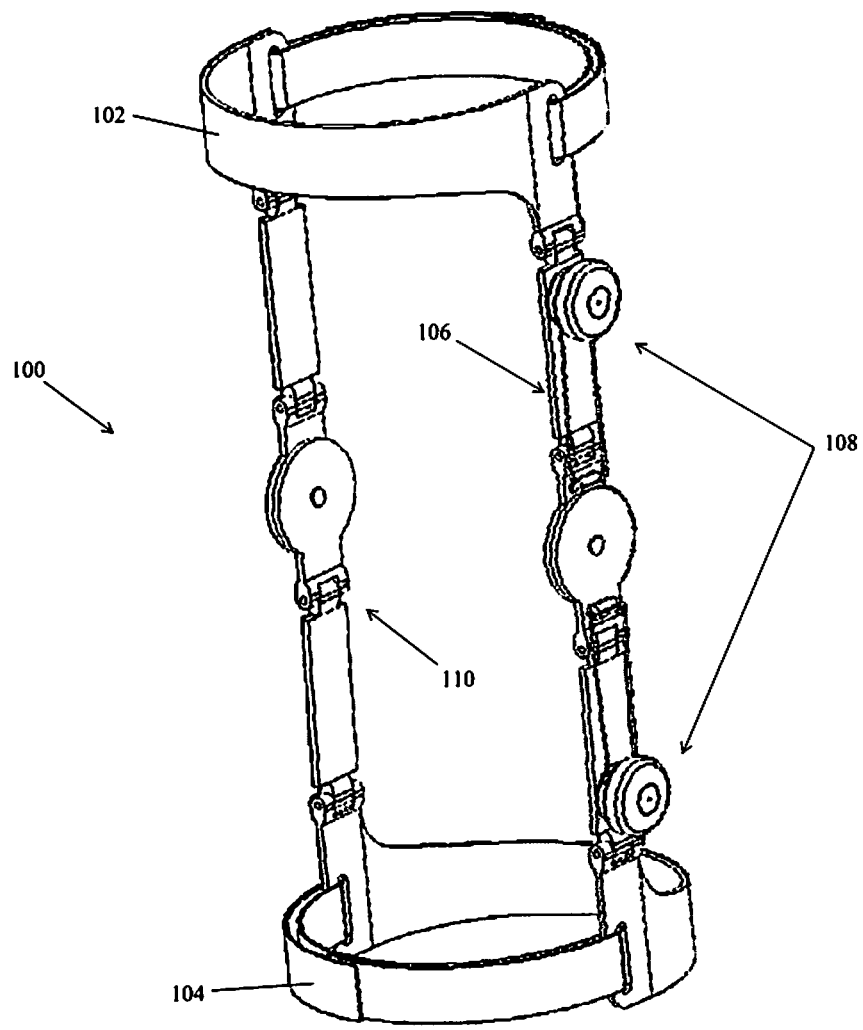
FIGS. 17-22 show a knee brace according to the disclosure.

For example, with reference to FIGS. 13 and 14, the cable reel 74 has been operated to tighten the cable 76 a degree to provide contracture to the wrist but to only slightly compress the bias member 86. The remaining compressibility of the bias member 86 enables a degree of movement of the wrist joint (either flexion or extension depending on the orientation of the wrist). In the event less movement of the wrist joint is desired, the cable may be further tightened to further move the movable member 88 closer to the blind end of the channel 84a and further compress the bias member 86, such as shown in FIGS. 15 and 16. In the event it is desired to provide no flexion or extension movement of the wrist, the cable reel 74 may be operated to tension the cable 76 such that the bias member 86 is fully compressed by the movable member 88.

Figure 18:
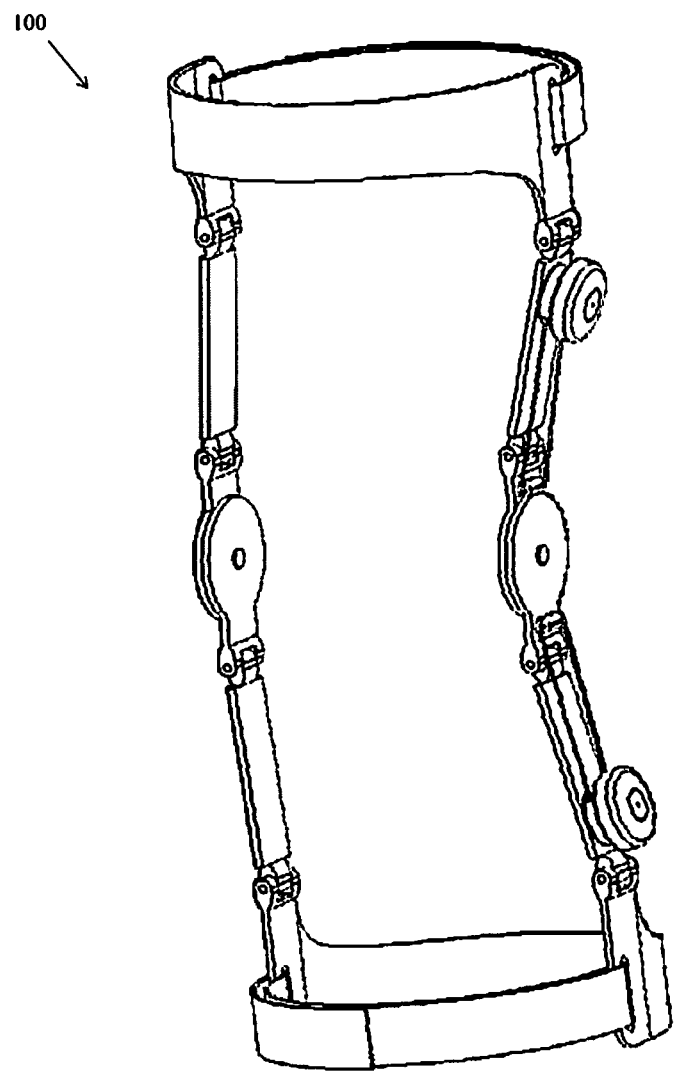

With reference to FIGS. 17-22, there is shown a knee brace 100 according to the disclosure. The knee brace 100 includes a thigh cuff 102, tibial cuff 104, and an upright assembly 106 having one or more cable reel systems 108 configured for adjusting the angulation of the upright 106. The knee brace 100 may optionally include an upright assembly 110 on the opposite side of the upright 106 that does not include a cable reel system. FIG. 18 shows the brace 100 having the cable reel system 108 adjusted to apply tension to the upright assembly 106 and impart an inward angulation to the upright assembly 106 and hence the brace 100. Absent such tension, the knee brace would maintain a relatively linear orientation.

Figure 19:
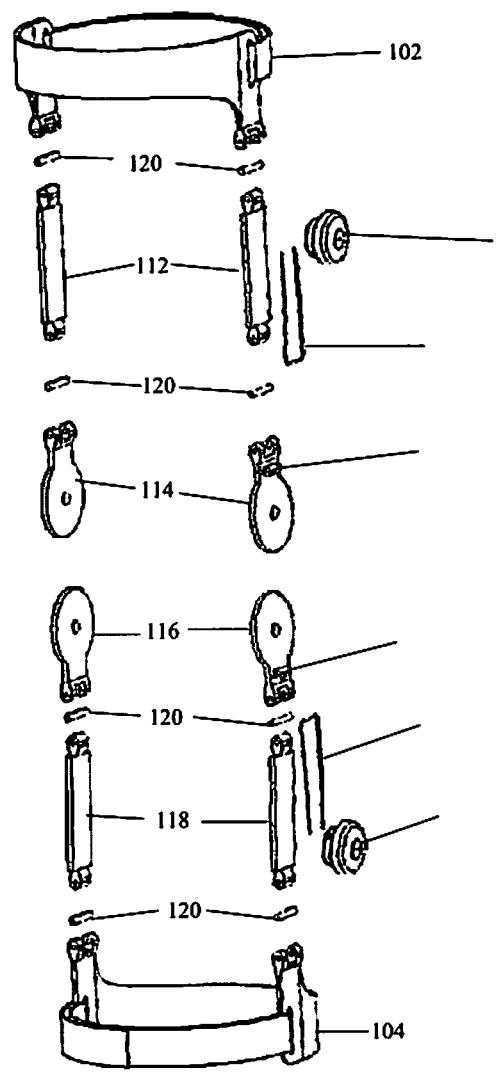
Figure 20:
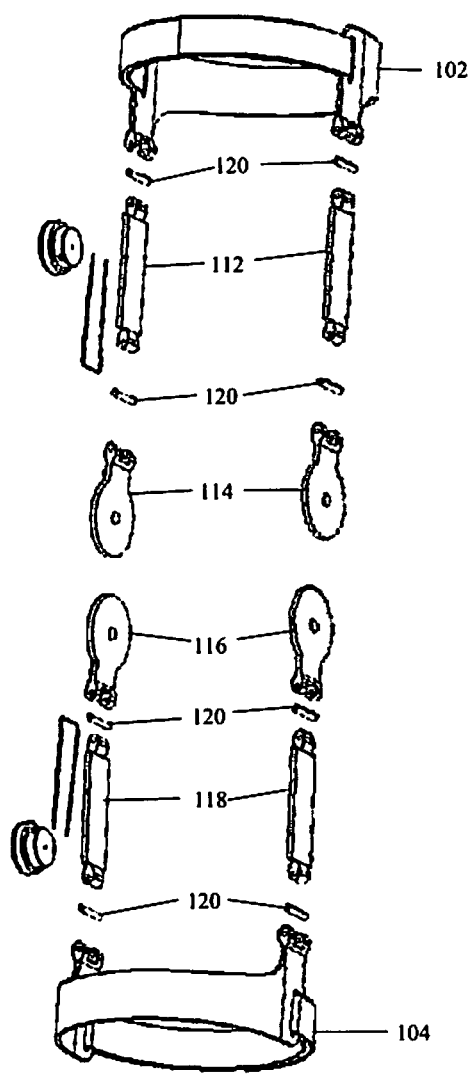

With reference to FIGS. 19 and 20, the upright assembly 106 and the upright assembly 110 each include rigid components pivotally joined to one another, and including a medial/lateral upright 112, a proximal joint 114 pivotally joined to a distal joint 116, and a medial/lateral upright 118. Pins 120 are used to pivotally connect the upright 112 to the thigh cuff 102 and the proximal knee joint 114, and the upright 118 to the tibial cuff 104 and the distal knee joint 116. The uprights 112 and 118, and the joints 114 and 116 are made of a rigid material such as aluminum.

Figure 21:
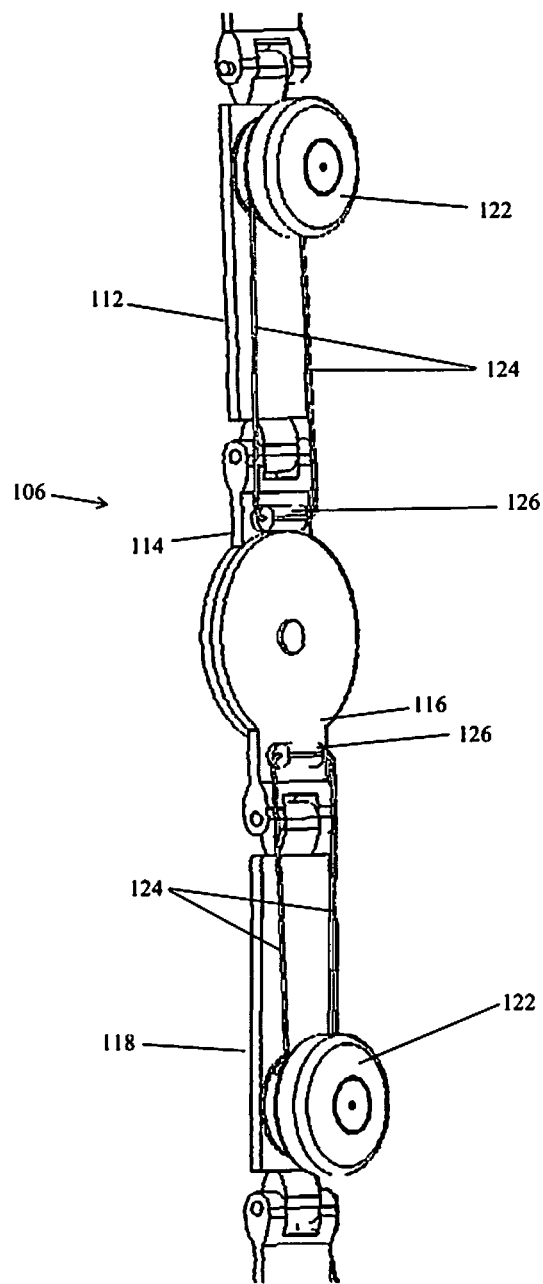
Figure 22:
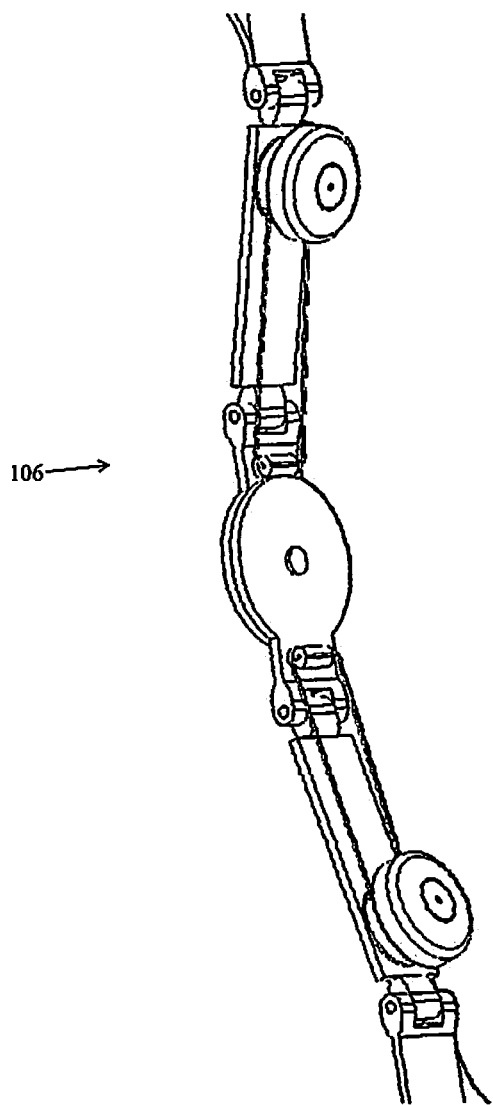

Each of the cable reel systems 108 includes a cable reel 122 mounted to the upright 106, a cable 124, and a cable guide 126 attached to the upright 106. The cable reel 122 is substantially similar to the reel 16. One of the cable reels 112 is preferably mounted to each of the uprights 112 and 118. The cable guide 126, as best seen in FIGS. 21 and 22, is configured as a cylinder attached to the distal joint and through which the cable 124 is trained. For example, a cable guide 126 is provided with the proximal joint 114 and the distal joint 116.

With further reference to FIG. 21, it will be seen that each of the cables 124 is relatively untensioned so that the relationship between the uprights and the joint is substantially linear. FIG. 22 represents a state in which the cables 124 are each tensioned to apply a tension between the uprights 112, 118 and the joints 114, 116 and impart a non-linear or angulated relationship between the uprights 112, 118 and the joints 114, 116.

By being able to change angulation above and or below the anatomical knee center it's possible to shift the weight of the knee medially and or laterally depending on which compartment needs to be unloaded. By shifting the weight on the knee joint medially and or laterally will open the joint on the damaged compartment while shifting the weight on the knee joint to the undamaged compartment easing the pain caused due to the osteoarthritis of bone on bone.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A brace for application to a body joint to maintain the joint in a substantially static position, the brace comprising:
   a substantially rigid brace member that substantially maintains its shape absent application of a substantial bending force and provides biomechanical support, stabilization and/or immobilization to the body joint to maintain the joint in a first substantially static position with virtually no range of motion; and
   a tensioning system connected to the brace member and including a tensionable member and a tensioning member each operatively associated with the brace member,
   wherein, the tensioning member is operable to adjustably impart tension to the tensionable member for applying a force to the brace member for adjusting the angulation of the brace as a function of the tension applied to the tensionable member to maintain the joint in a second and different substantially static position with virtually no range of motion and corresponding to the adjustment of the angulation of the brace.

2. The brace of claim 1, wherein the tensioning member comprises a cable reel and the tensionable member comprises a cable acted upon by the cable reel to tension the cable.

3. The brace of claim 2, wherein the cable reel is yieldably mounted to the brace member by a yieldable mount, comprising a base fixedly mounted to the brace member and having a channel, a movable member movably located within the channel, and a bias member located in the channel between the movable member and a blind end of the channel, wherein tension imparted to the cable by the cable reel determines the degree of compression of the bias member so as to yieldably mount the cable reel to the brace member.

4. The brace of claim 1, wherein the brace comprises a wrist brace.

5. The brace of claim 1, wherein the brace comprises a back brace.

6. The brace of claim 1, wherein the brace comprises a knee brace.

7. A brace structure, comprising:
   a substantially rigid brace substrate configured for application to a body joint and that substantially maintains a desired orientation of the brace structure absent application of a substantial bending force and provides biomechanical support, stabilization and/or immobilization to the body joint to maintain the joint in a first substantially static position with virtually no range of motion;
   a cable reel mounted to a first portion of the brace substrate;
   a cable operatively associated with the cable reel to wind and unwind the cable from the reel; and
   a cable guide fixed to the brace at a location apart from the cable reel, with the cable being trained through the cable guide and connected to the cable reel,
   wherein when the cable is substantially untensioned the brace structure is configured in a substantially linear orientation, and
   wherein when the cable reel is operated to tension the cable, the cable applies a force to the brace structure and the brace structure becomes angulated to a non-linear orientation as a function of the tension applied to the cable by the cable reel to maintain the joint in a second and different substantially static position with virtually no range of motion and corresponding to the adjustment of the angulation of the brace.

8. The brace of claim 7, wherein the cable reel is yieldably mounted to the brace substrate by a yieldable mount, the mount comprising a base fixedly mounted to the brace substrate and having a channel, a movable member movably located within the channel, and a bias member located in the channel between the movable member and a blind end of the channel, wherein tension imparted to the cable by the cable reel determines the degree of compression of the bias member so as to yieldably mount the cable reel to the brace substrate.

9. A brace for application to a body joint to maintain the joint in a substantially static position, the brace comprising:
   a substantially rigid one-piece brace member that substantially maintains its shape absent application of a substantial bending force and provides biomechanical support, stabilization and/or immobilization to the body joint to maintain the joint in a first substantially static position; and
   a tensioning system connected to the brace member and including a tensionable member and a tensioning member each operatively associated with the brace member,
   wherein, the tensioning member is operable to adjustably impart tension to the tensionable member for applying a force to the brace member for adjusting the angulation of the brace as a function of the tension applied to the tensionable member to maintain the joint in a second and different substantially static position with virtually no range of motion and corresponding to the adjustment of the angulation of the brace.

* * * * *